United States Patent [19]

Clapot et al.

[11] 4,240,823
[45] Dec. 23, 1980

[54] NEW PLANT GROWTH REGULATING COMPOSITIONS WHICH CONTAIN DERIVATIVES OF N-ACYL METHIONINE

[75] Inventors: Claude Clapot, Oullins; Jean Vial, Dardilly; Jacqueline Mourier, Lyons; Jean C. Boch, Neris les Bains, all of France

[73] Assignee: Philagro S.A., Lyons, France

[21] Appl. No.: 773,278

[22] Filed: Mar. 1, 1977

[30] Foreign Application Priority Data

Mar. 24, 1976 [FR] France ............... 76 09242

[51] Int. Cl.³ ............... A01N 43/08; A01N 43/40; A01N 37/34; A01N 31/04
[52] U.S. Cl. ............... 71/98; 71/76; 71/88; 71/94; 260/347.2; 260/404; 260/464; 260/465 D; 260/465.4; 546/316; 560/16; 560/153; 560/250; 562/426; 562/427; 562/430; 562/506; 562/507; 562/556; 564/154
[58] Field of Search ............... 71/98, 88, 94, 103; 560/16

[56] References Cited

U.S. PATENT DOCUMENTS

| | | | |
|---|---|---|---|
| 2,734,816 | 2/1956 | Wood et al. | 71/98 |
| 2,840,595 | 6/1958 | Stevens | 71/98 X |
| 3,209,002 | 9/1965 | Galat | 424/249 X |
| 3,459,533 | 8/1969 | Weesner | 71/98 |
| 3,671,212 | 6/1972 | Jaworski | 71/98 X |

FOREIGN PATENT DOCUMENTS 782037 4/1972 Belgium.
1466141 12/1966 France.
1518665 2/1968 France.

OTHER PUBLICATIONS

Wood et al., J. Org. Chem., 17 (1952), 891-896.
C.A., 52 (1958), Pal et al., 11171 ef.
C.A., 52 (1958), Ronwin, 5292f to 5293c.
C.A., 63 (1965), Kazmierczak et al., 16450g.
C.A., 60 (1964), Alekseeva et al., 4249e.

Primary Examiner—Joseph Paul Brust
Attorney, Agent, or Firm—Browdy and Neimark

[57] ABSTRACT

Compounds of the formula:

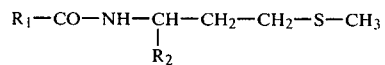

in which $R_1$ is hydrogen, optionally halogenated alkyl, optionally halogenated cycloalkyl, optionally halogenated alkenyl, optionally halogenated aralkenyl or aryloxyalkenyl mono or bicyclic aryl (optionally substituted by halogen, alkyl, trifluoromethyl, nitro, cyano, amino, hydroxyl, alkoxy, aminosulphonyl or alkylcarbonyloxy), or monocyclic or bicyclic heterocyclic of 5-11 chain members and having one or two heteroatoms (optionally substituted), and $R_2$ is a carboxylic acid group or a salt or ester thereof, is found to have plant growth regulating activity.

15 Claims, No Drawings

NEW PLANT GROWTH REGULATING COMPOSITIONS WHICH CONTAIN DERIVATIVES OF N-ACYL METHIONINE

The present invention relates to new plant growth-regulating compositions which contain derivatives of N-acylmethionine as the active material. It also relates to new derivatives of N-acylmethionine which can be used for the preparation of compositions according to the invention.

The term "growth regulator" here has the meaning usually accepted in the French language, which corresponds to "growth substance" in the Anglo-Saxon literature, the term growth relating to the production of living matter and not simply to the change in the height of the plants. Accordingly, "growth regulator" is, in the text which follows, to be understood as meaning products capable of modifying the physiology of the plants in various ways.

It has already been proposed (compare Belgian Pat. No. 782,037) to use methionine and certain of its esters as growth regulators; however, these compounds frequently have insufficient effects to enable them to be used industrially.

It has also been proposed to use, as growth regulators, N-phenoxyacetyl or N-phenylacetyl derivatives of numerous aminoacids, amongst which methionine is mentioned (compare J. Org. Chem. 17, p. 891-6, 1952).

The mode of action of these compounds on the plants is similar to that of the other derivatives of phenoxyacetic and phenylacetic acids, these being compounds well-known for their phytohormonal and herbicidal action.

The present invention relates to plant growth-regulating compositions which contain, as the active material, at least one compound corresponding to the general formula

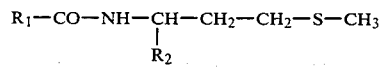

$$R_1-CO-NH-CH(R_2)-CH_2-CH_2-S-CH_3 \quad (I)$$

in which: $R_1$ represents a hydrogen atom, an optionally halogenated ($C_1$ to $C_{20}$) alkyl radical, an optionally halogenated ($C_3$ to $C_6$) cycloalkyl radical, an optionally halogenated ($C_2$ to $C_{20}$) alkenyl radical, an optionally halogenated aralkenyl or aryloxyalkenyl radical (with a $C_2$ to $C_4$ alkenyl part), a monocyclic or bicyclic aryl radical optionally substituted by one or more identical or different atoms or radicals from amongst halogen atoms, ($C_1$ to $C_4$) alkyl radicals, trifluoromethyl, nitro, cyano, optionally substituted amino, hydroxyl, alkoxy (with a $C_1$ to $C_4$ alkyl part), aminosulphonyl or alkylcarbonyloxy (with a $C_1$ to $C_4$ alkyl part), or a monocyclic or bicyclic heterocyclic radical containing from 1 to 2 hetero-atoms and from 5 to 11 chain members, this radical being optionally substituted, and $R_2$ represents a carboxylic acid group or a salt which this group can form with a conventional inorganic base or with a primary, secondary or tertiary amine or alkanolamine, a

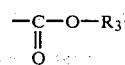

group, in which $R_3$ is a ($C_1$ to $C_4$) alkyl radical optionally substituted by one or more hydroxyl groups, a —CN group or a

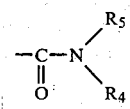

group in which $R_4$ and $R_5$, which may be identical or different, represent a hydrogen atom or a ($C_1$ to $C_4$) alkyl radical.

The invention preferably relates to compositions which contain, as the active material, at least one compound corresponding to the general formula (II):

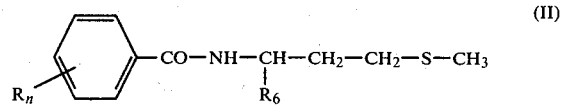

in which: $R_n$ represents from 1 to 3 identical or different atoms or radicals chosen from amongst halogen atoms, ($C_1$ to $C_4$) alkyl radicals, trifluoromethyl, nitro, optionally acylated amino, hydroxyl, alkoxy (with a $C_1$ to $C_4$ alkyl part) or alkoxycarbonyloxy (with a $C_1$ to $C_4$ alkyl part), and $R_6$ represents a carboxylic acid group or a salt obtained by the action of the said acid on an inorganic base or on a primary, secondary or tertiary amine or on an alkanolamine, a

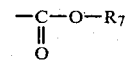

group, in which $R_7$ is a $C_1$ to $C_4$ alkyl radical, a

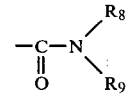

group, in which $R_8$ and $R_9$, which may be identical or different, are a hydrogen atom or a methyl or ethyl radical, or a —CN group.

In addition, the invention relates to new compounds of the general formula (III):

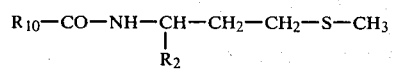

in which: $R_{10}$ represents a monocyclic or bicyclic aryl radical optionally substituted by one or more atoms or radicals from amongst halogen atoms or ($C_1$ to $C_4$) alkyl, trifluoromethyl, nitro, cyano, optionally substituted amino, hydroxyl, alkoxy (with a $C_1$ to $C_4$ alkyl part) radical, and $R_2$ has the same meaning as in formula I.

Several of the compounds according to formula I have already in themselves been described in the literature.

Thus, it is already known, from French Pat. No. 1,518,665 to prepare the N-acyl-aminoacides of the general formula

R—CO—NH—R'—COOH in which R represents a saturated or unsaturated aliphatic chain which can contain from 1 to 30 carbon atoms, by reaction of an acid or an acid chloride or an acid anhydride with an aminoacid. The compounds obtained can be used as detergents for body hygiene.

Equally, French Pat. No. 1,466,141 describes the preparation of N-acetyl-methionine of the formula:

$$CH_3-CO-NH-\underset{\underset{COOH}{|}}{CH}-CH_2-CH_2-S-CH_3$$

and the use of this compound for skin care.

However, as far as presently known, none of the compounds which form the subject of the present application have ever been described as plant growth regulators.

Several processes can be used for the preparation of the compounds which form the subject of the present invention.

The compounds for which $R_2$ represent a carboxylic acid group are prepared in accordance with a method described in the literature, which consists of an acylation reaction of (DL)-methionine by means of an acid anhydride or an acid chloride in the presence of an HCl acceptor. This reaction is generally carried out in water at ambient temperature in the presence of sodium hydroxide.

The compounds thus obtained can be rendered insoluble by reacidification. When the acid chloride contains a saponifiable or hydrolysable group it is however preferable to carry out the reaction in a non-aqueous medium so as not to modify this group.

Under these conditions, the methionine is first treated with sodium methylate in methanol and the sodium salt of methionine, thus obtained, is isolated by concentration.

This sodium salt is then condensed with the acid chloride in an aprotic solvent medium, for example in acetone.

The compounds for which $R_2$ represents a $$-\overset{\overset{O}{\|}}{C}-O-R_3$$

group are obtained by esterification of the corresponding acids by simple boiling of the acid with a large excess of alcohol, in the presence of a strong acid catalyst such as hydrochloric acid, sulphuric acid or p-toluenesulphonic acid.

The preparation of the methyl or ethyl esters of the compounds for which $R_2$ represents a carboxylic acid group is thus carried out by first dissolving these compounds respectively in methanol or ethanol. After introducing anhydrous hydrogen chloride gas until saturation is reached, this solution or dispersion is heated to the boil and then kept at the boil for two hours. The excess alcohol is then removed under reduced pressure and the residue obtained is washed copiously with water. It can be distilled if it is liquid or crystallised from a suitable solvent if it is solid.

If it is desired to esterify these acids by means of less volatile alcohols, such as n-butanol or glycerol, the chosen acid and alcohol can be dissolved in a solvent such as toluene, the process being carried out in the presence of p-toluenesulphonic acid. The whole is heated under reflux in a reactor equipped with a Dean and Stark type of device. The water formed is entrained by azeotropic distillation and can be removed continuously. When the reaction has been completed, the cold solution is washed with water until neutral and then concentrated to dryness. The residue can be distilled or recrystallised depending on whether it is liquid or solid.

The compounds for which $R_2$ represents a —CN group are obtained by acylation of 2-amino-4-methylthio-butyronitrile:

$$NH_2-\underset{\underset{CN}{|}}{CH}-CH_2-CH_2-S-CH_3$$

by means of an acid anhydride or acid chloride.

To carry out this process it is possible, for example, to dissolve the acid chloride in toluene and run this solution dropwise into a solution of 2-amino-4-methylthio-butyronitrile and triethylamine in toluene, whilst keeping the temperature below or at 30° C. The solution is then stirred at ambient temperature after which the triethylamine hydrochloride is filtered off. The filtrate is then concentrated to dryness and the residue is recrystallised from a suitable solvent.

2-Amino-4-methylthio-butyronitrile is a known compound which can be prepared by any one of the methods described in the literature, for example the method of J. R. CATCH, A. H. COOK and A. R. GRAHAM (Nature 159, p. 578 (1947)) or the method of D. O. HOLLAND and H. H. C. NALER (J. Chem. Soc. p. 3,403, 1952).

The compounds for which $R_2$ represents a $$-CO-N\overset{R_4}{\underset{R_5}{\diagdown}}$$

group are obtained from the compounds for which $R_2$ represents a $$-\overset{\overset{O}{\|}}{C}-O-R_3$$

group by subjecting the latter to an ammonolysis or aminolysis reaction, by treating them respectively either with ammonia or with an amine, in an aqueous or alcoholic medium.

The examples which follow are given without implying a limitation, in order to illustrate the preparation of the compounds which can be used according to the invention, and in order to demonstrate their plant growth-regulating properties.

All the compounds corresponding to the general formula (I) possess at least one asymmetrical carbon and can thus exist in several optical isomer forms which possess a dextrogyratory or laevogyratory optical rotation.

EXAMPLES 1 TO 40

Preparation of the compounds for which $R_2$ is a carboxylic acid group:

EXAMPLE 1: Preparation of (DL)-2-(3',5'-dichloro-benzamido)-4-methylthio-butyric acid.

(DL)-Methionine (1 mol = 149 g.) is dissolved in water (one liter) containing sodium hydroxide (88 g. = 2.2 mols). Furthermore, 3,5-dichlorobenzoyl chloride (1 mol = 209.5 g.) is dissolved in diethyl ether (500 cc.). The solution containing the acid is then run dropwise into the preceding aqueous solution, which is kept under turbulent stirring, at a temperature below 30° C. When all has been added, the aqueous layer is decanted and then reacidified to PH = 1 by means of concentrated hydrochloric acid.

The (DL)-2-(3',5'-dichloro-benzamido)-4-methylthiobutyric acid precipitates and is then filtered off, washed with water, dried and recrystallised from methanol.

Yield: 89% (of product recrystallised from methanol).

Melting point: 167.7° C.

Percentage analysis for $C_{12}H_{13}Cl_2NO_3S = 322$

|  | C % | H % | N % |
|---|---|---|---|
| Calculated | 44.72 | 4.04 | 4.35 |
| Found | 44.80 | 4.06 | 4.26 |

EXAMPLES 2 TO 45

The procedure of Example 1 is followed for all the examples with the exception of Examples 28 and 29, for which the acid chloride starting material contains hydrolysable groups. In these Examples 28 and 29, the methionine is first treated with one molecular equivalent of sodium methylate in methanol. After concentration by evaporation, the sodium salt of methionine is treated with the acid chloride in acetone at 60° C. for one hour. The acetone is then evaporated and the residue is recrystallised from a mixture of ether and pentane.

The characteristics of the products obtained according to these Examples 2 to 45, as well as the yields, are indicated in the table which follows.

|  | $R_1$ | $R_2$ | Empirical formula | Molecular weight | Melting point | Yield | Percentage analysis C % H % N % |
|---|---|---|---|---|---|---|---|
| Ex. 2 | $CH_3-(CH_2)_6-$ | —COOH | $C_{13}H_{25}NO_3S$ | 275 | 80.5° C. | 90.9% | C: 56.73 9.09 5.09<br>F: 56.85 9.12 5.14 |
| Ex. 3 | 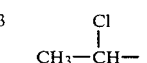 | —COOH | $C_8H_{14}ClNO_3S$ | 239.5 | 94.7° C. | 37.6% | C: 40.08 5.85 5.85<br>F: 40.07 5.91 5.83 |
| Ex. 4 | 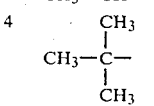 | —COOH | $C_{10}H_{19}NO_3S$ | 233. | 82.9° C. | 25.8% | C: 51.50 8.15 6.00<br>F: 51.57 8.19 6.06 |
| Ex. 5 | $CH_3-CH=CH-$ | —COOH | $C_9H_{15}NO_3S$ | 217 | 153.9° C. | 55% | C: 49.77 6.91 6.45<br>F: 49.63 6.97 6.40 |
| Ex. 6 | 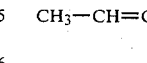 | —COOH | $C_9H_{15}NO_3S$ | 217 | 109° C. | 46% | C: 49.77 6.91 6.45<br>F: 49.77 7.10 6.54 |
| Ex. 7 | 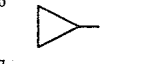 | —COOH | $C_{13}H_{23}NO_3S$ | 273 | 110° C. | 44.7% | C: 57.14 8.42 5.13<br>F: 57.14 8.44 4.48 |
| Ex. 8 | 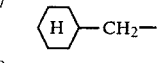 | —COOH | $C_{14}H_{16}ClNO_3S$ | 313.5 | 192° C. | 89.7% | C: 53.59 5.10 4.47<br>F: 53.60 5.13 4.45 |
| Ex. 9 | 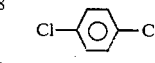 | —COOH | $C_{12}H_{25}NO_3S$ | 253 | 152.5° C. | 75% | C: 56.92 5.93 5.53<br>F: 56.96 5.19 5.54 |
| Ex. 10 | 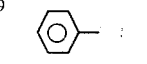 | —COOH | $C_{12}H_{14}ClNO_3S$ | 287.5 | 139° C. | 80% | C: 50.08 4.86 4.86<br>: 50.38 4.88 4.86<br>F: 50.47 4.88 4.92 |
| Ex. 11 | 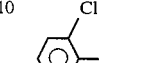 | —COOH | $C_{12}H_{14}FNO_3S$ | 271 | 96° C. | 66.5% | C: 53.14 5.17 5.17<br>F: 53.38 5.32 5.29<br>53.10 5.26 5.11 |
| Ex. 12 | 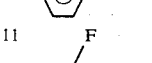 | —COOH | $C_{12}H_{14}ClNO_3S$ | 287.5 | 150.4° C. | 94% | C: 50.09 4.87 4.87<br>F: 50.20 4.97 5.24 |
| Ex. 13 | 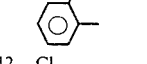 | —COOH | $C_{12}H_{14}BrNO_3S$ | 332 | 154° C. | 90.9% | C: 43.37 5.12 4.22<br>F: 43.50 4.99 4.14 |
| Ex. 14 | 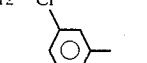 | —COOH | $C_{12}H_{14}FNO_3S$ | 271 | 120–2° C. | 86.5% | C: 5.17<br>F: 5.18 |
| Ex. 15 | 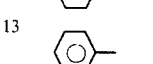 | —COOH | $C_{12}H_{13}Cl_2NO_3S$ | 322 | 81.1° C. | 82.6% | C: 44.72 4.04 4.35<br>F: 44.80 4.02 4.41 |

-continued

| | R₁ | R₂ | Empirical formula | Molecular weight | Melting point | Yield | Percentage analysis | | |
|---|---|---|---|---|---|---|---|---|---|
| Ex. 16 | 2,4-dichlorophenyl | —COOH | $C_{12}H_{13}Cl_2NO_3S$ | 322 | 136.5° C. | 82.9% | C: 44.72 4.04 4.35<br>F: 44.80 4.36 4.26 | | |
| Ex. 17 | 2-chloro-4-fluorophenyl | —COOH | $C_{12}H_{13}ClFNO_3S$ | 305.5 | 147° C. | 78.8% | C: 47.14 4.25 4.58<br>F: 47.04 4.23 4.71 | | |
| Ex. 18 | 2-methylphenyl | —COOH | $C_{13}H_{17}NO_3S$ | 267 | 129.5° C. | 68% | C: 58.43 6.37 5.24<br>F: 58.46 6.25 5.20 | | |
| Ex. 19 | 3-methylphenyl | —COOH | $C_{13}H_{17}NO_3S$ | 267 | 143.8° C. | 43% | C: 58.43 6.37 5.24<br>F: 58.24 6.26 5.30 | | |
| Ex. 20 | 4-tert-butylphenyl ((CH₃)₃C—) | —COOH | $C_{16}H_{23}NO_3S$ | 308 | 122.2° C. | 91.8% | C: 62.14 7.44 4.53<br>F: 62.20 7.18 4.63 | | |
| Ex. 21 | 2-methoxyphenyl (OCH₃) | —COOH | $C_{13}H_{17}NO_4S$ | 283 | 94° C. | | C:  4.95<br>F:  4.75 | | |
| Ex. 22 | 3-trifluoromethylphenyl (CF₃) | —COOH | $C_{13}H_{14}F_3NO_3S$ | 321 | 110° C. | | C:  4.35<br>F:  4.40 | | |
| Ex. 23 | 2-nitrophenyl (NO₂) | —COOH | $C_{12}H_{14}N_2O_5S$ | 298 | 122–124° C. | | N % S %<br>C: 9.38 10.74<br>F: 9.22 10.70 | | |
| Ex. 24 | 3-nitrophenyl (NO₂) | —COOH | $C_{12}H_{14}N_2O_5S$ | 298 | 129–130° C. | 76.3% | C % H % N %<br>C: 48.32 4.70 9.40<br>F: 49.01 4.76 9.39 | | |
| Ex. 25 | 2-chloro-4-isopropylphenyl | —COOH | $C_{15}H_{20}ClNO_3S$ | 329.5 | 146° C. | 92.4% | C: 54.63 6.07 4.25<br>F: 54.57 5.96 4.14 | | |
| Ex. 26 | 2,4-dihydroxyphenyl (OH, OH) | —COOH | $C_{12}H_{15}NO_5S$ | 285 | 150–155° C. | | N %<br>C: 4.90<br>F: 4.72 | | |
| Ex. 27 | 2-hydroxy-4-methoxyphenyl (OH, OCH₃) | —COOH | $C_{13}H_{17}NO_5S$ | 299 | 127° C. | | N % S %<br>C: 5  11.48<br>F: 4.29 10.20 | | |
| Ex. 28 | 2,4-diacetoxyphenyl (OCOCH₃, OCOCH₃) | —COOH | $C_{16}H_{19}NO_7S$ | 369 | 90° C. | | N %<br>C: 3.82<br>F: 3.14 | | |
| Ex. 29 | 2,3-diacetoxyphenyl (OCOCH₃, OCOCH₃) | —COOH | $C_{16}H_{19}NO_7S$ | 369 | 115° C. | | N % S %<br>C: 3.82 8.7<br>F: 3.44 8.32 | | |

-continued

| | R₁ | R₂ | Empirical formula | Molecular weight | Melting point | Yield | Percentage analysis | | |
|---|---|---|---|---|---|---|---|---|---|
| Ex. 30 | 2-methyl-phenol (CH₃, OH on benzene) | —COOH | $C_{13}H_{17}NO_4S$ | 283 | 155° C. | | | N %<br>C: 4.94<br>F: 4.86 | |
| Ex. 31 | Br, OH on benzene | —COOH | $C_{12}H_{14}BrNO_4S$ | 348 | 125° C. | | C: | N %<br>4.02<br>4.04 | Br %<br>23<br>22.6 |
| Ex. 32 | OCH₃, SO₂NH₂ on benzene | —COOH | $C_{13}H_{18}N_2O_6S_2$ | 330 | 110° C. | | C: | N %<br>7.73<br>7.55 | S %<br>17.70<br>17.48 |
| Ex. 33 | naphthyl | —COOH | $C_{16}H_{17}NO_3S$ | 303 | 120° C. | 90% | C:<br>F: | C %<br>64.68<br>64.59 | H %<br>5.61<br>5.70 | N %<br>4.62<br>4.56 |
| Ex. 34 | furyl (methylfuran) | —COOH | $C_{10}H_{13}NO_4S$ | 243 | 132° C. | 77.3% | C:<br>F: | C %<br>49.38<br>49.50 | H %<br>5.35<br>5.54 | N %<br>5.76<br>5.74 |
| Ex. 35 | pyridylmethyl | —COOH | $C_{11}H_{14}N_2O_3S$ | 254 | 218.5° C. | 14.1% | C:<br>F: | C %<br>51.97<br>52.05 | H %<br>5.51<br>5.46 | N %<br>11.02<br>11.06 |
| Ex. 36 | 3-CF₃-C₆H₄-CO-NH-C₆H₃(OH)- | —COOH | $C_{20}H_{19}F_3N_2O_5S$ | 456 | 73° C. | | C: | N %<br>6.14<br>5.62 | F %<br>12.5<br>13.0 |
| Ex. 37 | 3-F-C₆H₄-CO-NH-C₆H₃(OH)- | —COOH | $C_{19}H_{19}FN_2O_5S$ | 406 | 80° C. | | C:<br>F: | C %<br>56.15<br>55.03 | H %<br>4.71<br>4.62 | N %<br>6.90<br>5.95 |
| Ex. 38 | 4-F-C₆H₄-CO-NH-C₆H₃(OH)- | —COOH | $C_{19}H_{19}FN_2O_5S$ | 406 | 110° C. | | C: | N %<br>6.90<br>5.98 | S %<br>4.68<br>4.96 |
| Ex. 39 | 2-F-C₆H₄-CO-NH-C₆H₃(OH)- | —COOH | $C_{19}H_{19}FN_2O_5S$ | 406 | 165° C. | | C:<br>F: | N %<br>6.90<br>6.85 | F %<br>7.90<br>7.60 | S %<br>4.68<br>4.66 |
| Ex. 40 | C₆H₅—CH=CH— | —COOH | $C_{14}H_{17}NO_3S$ | 279 | 172° C. | 83.8% | C:<br>F: | C %<br>60.21<br>60.26 | H %<br>6.09<br>6.12 | N %<br>5.02<br>5.11 |

EXAMPLES 41 to 52

Preparation of the compounds for which $R_2$ is a carboxylic acid ester group.

EXAMPLE 41: Preparation of (DL)-ethyl 2-(3',5'-dichloro-benzamido)-4-methylthio-butyrate, the ethyl ester of the compound according to Example 1.

The compound (1 mol = 322 g.) obtained in Example 1 is used as the starting material and dissolved in absolute ethanol (500 cc.). Anhydrous hydrogen chloride gas is introduced into the solution until saturation is reached. This solution is then raised to the boil and kept at the boil for two hours. The excess alcohol is then removed under reduced pressure and the residue obtained is washed with water until neutral. The ethyl ester obtained is then recrystallised from ethyl acetate.

Yield: 85.7% (of recrystallised product)
Melting point: 90.1° C.
Percentage analysis for $C_{14}H_{17}Cl_2NO_3S = 350$

|  | C % | H % | N % |
|---|---|---|---|
| Calculated | 48.00 | 4.86 | 4.00 |
| Found | 48.09 | 4.98 | 4.05 |

EXAMPLES 42 to 51

The procedure of Example 41 is followed. The characteristics of the products obtained as well as the yields are indicated in the table below.

| | $R_1$ | $R_2$ | Empirical formula | Molecular weight | Melting point | Yield | Percentage analysis |
|---|---|---|---|---|---|---|---|
| | | | | | | | C %   H %   N % |
| Ex. 42 | $CH_3-CH_2-$ | $-COOC_2H_5$ | $C_{10}H_{19}NO_3S$ | 233 | 61° C. | 36.4% | C: 51.50  8.15  6.01<br>F: 51.61  8.14  6.01 |
| Ex. 43 | phenyl-CH=CH- | $-COOC_2H_5$ | $C_{16}H_{21}NO_3S$ | 307 | 114° C. | 96.7% | C: 62.54  6.84  4.86<br>F: 62.63  6.93  4.79 |
| Ex. 44 | 2-Cl-phenyl | $-COOC_2H_5$ | $C_{14}H_{18}ClNO_3S$ | 315.5 | Bp 172-5° C./0.004 mm Hg | 84.5% | C: 53.35  5.71  4.44<br>F: 53.49  5.86  4.42<br>   53.20  5.78  4.47 |
| Ex. 45 | 4-Cl-phenyl | $-COOC_2H_5$ | $C_{14}H_{18}ClNO_3S$ | 315.5 | 62.1° C. | 63.4% | C: 53.25  5.70  4.44<br>F: 53.36  6.08  4.99 |
| Ex. 46 | Cl,F-phenyl | $-COOC_2H_5$ | $C_{14}H_{17}ClFNO_3S$ | 333.5 | 112° C. | 79.5% | C: 50.37  5.09  4.19<br>F: 50.42  5.19  4.34 |
| Ex. 47 | OH-phenyl | $-COOCH_3$ | $C_{13}H_{17}NO_4S$ | 283 | 63° C. | | |
| Ex. 48 | $NO_2$-phenyl | $-COOC_2H_5$ | $C_{14}H_{18}N_2O_5S$ | 326 | Bp 150° C. | 52.4% | C: 51.33  5.52  8.59<br>F: 51.40  5.84  8.56 |
| | | | | | | | N %   S % |
| Ex. 49 | $OCH_3$,$SO_2-NH_2$-phenyl | $-COOC_2H_5$ | $C_{15}H_{22}N_2O_6S_2$ | 390 | 157° C. | | C: 7.19  16.45<br>F: 7.10  16.45 |
| | | | | | | | C %   H %   N % |
| Ex. 50 | furyl | $-COO-C_2H_5$ | $C_{12}H_{17}NO_4S$ | 271 | Bp 120° C. | 69.7% | C: 53.14  6.27  5.17<br>F: 53.04  6.18  5.04 |
| | | | | | | | N %   F %   S % |
| Ex. 51 | OH, F-phenyl-CO-NH-phenyl | $-COOC_2H_5$ | $C_{21}H_{23}FN_2O_5S$ | 434 | 110° C. | | C: 6.45  4.38  7.38<br>F: 5.84  4.82  6.88 |

EXAMPLE 52: Preparation of (DL)-n-butyl 2-(3',5'-dichloro-benzamido)-4-methylthio-butyrate.

The starting materials of the compound (one mol = 322 g.) obtained in Example 1 and n-butanol (1.5 mols = 74 g.), which are dissolved in toluene (500 cc.) in the presence of p-toluenesulphonic acid (2 g.).

The whole is heated under reflux in a reactor equipped with a device of the Dean and Stark type.

The water formed by the reaction is entrained by azeotropic distillation and is removed continuously.

When the reaction has ended, the cold solution is washed with water until neutral and then concentrated to dryness. The residue is then recrystallised.

Yield: 87.5%
Melting point: 73.4° C.
Percentage analysis for $C_{16}H_{21}Cl_2N_1O_3S$

|  | C % | H % | N % |
|---|---|---|---|
| Calculated | 50.79 | 5.55 | 3.70 |
| Found | 50.96 | 5.63 | 3.67 |

EXAMPLES 53 to 56

Preparation of the compounds for which $R_2$ is a —CN group.

EXAMPLE 53: Preparation of (DL)-2-(3',5'-dichloro-benzamido)-4-methylthio-butyronitrile.

3,5-Dichloro-benzoyl chloride (one mol=209.5 g.) is dissolved in toluene (500 cc.) and this solution is run dropwise into a solution of 2-amino-4-methylthio-butyronitrile (1 mol=130 g.) and triethylamine (1 mol=101 g.).

During this running-in stage, the temperature is kept below or at 30° C. by external cooling. When all has been added, the reactants are stirred for 30 minutes at ambient temperature after which the triethylamine hydrochloride is filtered off.

The filtrate is then concentrated to dryness and the residue is recrystallised from ethanol.
Yield: 65.5%
Melting point: 137.8° C.
Percentage analysis for $C_{12}H_{12}Cl_2N_2OS$

|  | C % | H % | N % |
|---|---|---|---|
| Calculated | 47.52 | 3.96 | 9.24 |
| Found | 47.68 | 4.01 | 9.28 |

EXAMPLES 54 to 56

The procedure of Example 53 is followed. The results obtained are indicated in the table below.

| | $R_1$ | $R_2$ | Empirical formula | Molecular weight | Melting point | Yield | | Percentage analysis C % | H % | N % |
|---|---|---|---|---|---|---|---|---|---|---|
| Ex. 54 | Cl—CH$_2$— | —CN | $C_7H_{11}ClN_2OS$ | 206.5 | 64° C. | 62% | C: | 40.68 | 5.33 | 13.56 |
|  |  |  |  |  |  |  | F: | 40.89 | 4.93 | 13.76 |
| Ex. 55 | CCl$_3$— | —CN | $C_7H_9Cl_3N_2OS$ | 275.5 | $n_D^{20}$ = 1.5377 | 83% | C: | 30.49 | 3.27 | 10.16 |
|  |  |  |  |  |  |  | F: | 30.76 | 3.26 | 10.22 |
| Ex. 56 | Cl—C$_6$H$_4$— | —CN | $C_{12}H_{13}ClN_2OS$ | 268.5 | 95° C. | 58% | C: | 53.63 | 4.84 | 10.43 |
|  |  |  |  |  |  |  | F: | 53.80 | 4.95 | 10.41 |

EXAMPLES 57 and 58:

Preparation of the compounds for which $R_2$ is a

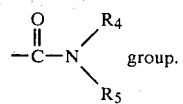 group.

EXAMPLE 57: Preparation of (DL)-2-(3',5'-dichloro-benzamido)-4-methylthio-butyramide.

The starting material is (DL)-ethyl 2-(3',5'-dichloro-benzamido)-4-methylthio-butyrate, the preparation of which is described in Example 41. This compound (0.3 mol) is dissolved in absolute alcohol (150 cc.). The solution is saturated with ammonia at a temperature of 5° C. and is then heated for two hours at 90° C. After cooling, the compound obtained is recrystallised from ethyl acetate.
Yield: 31.2%
Melting point: 221.3° C.
Percentage analysis for $C_{12}H_{14}Cl_2N_2O_2S$

|  | C % | H % | N % |
|---|---|---|---|
| Calculated | 48.14 | 5.16 | 8.02 |
| Found | 47.2 | 5.3 | 8.3 |

Example 58: Preparation of (DL)-2-(3',5'-dichloro-benzamido)-4-methylthio-N-ethylbutyramide.

The procedure of Example 57 is followed, replacing the ammonia treatment by a treatment with $NH_2-C_2H_5$.
Yield: 87.6%
Melting point: 140° C.
Percentage analysis for $C_{14}H_{18}Cl_2N_2O_2S$

|  | C % | H % | N % |
|---|---|---|---|
| Calculated | 48.14 | 5.16 | 8.02 |
| Found | 47.3 | 5.3 | 8.3 |

EXAMPLES 59 to 62

| Example | $R_1$ | $R_2$ |
|---|---|---|
| Ex. 59 | CH$_3$— | —COOH |
| Ex. 60 | CH$_3$—(CH$_2$)$_7$—CH=CH—(CH$_2$)$_7$— | —COO—CH$_2$—CH—CH$_2$<br>　　　　　　OH　OH |
| Ex. 61 | CH$_3$—(CH$_2$)$_{16}$— | —COOH |
| Ex. 62 | —CH$_3$—(CH$_2$)$_{16}$— | —COO—CH$_2$—CH—CH$_2$<br>　　　　　　OH　OH |

These four compounds are known compounds, the preparation of which has been described in the literature.

Compound No. 59 is known for its use as a detergent for body hygiene. Compounds 60, 61 and 62 are known as emulsifiers which can be used in the foodstuff, cosmetic and pharmaceutical fields.

The biological properties of the compounds according to the invention are demonstrated by tests in which the plants are treated in accordance with several methods. In the text which follows, "solution" is to be understood either as an aqueous solution, if the material is water-soluble, or, if it is not, as an aqueous dispersion of a wettable powder, containing 20% of active material, or as an emulsifiable concentrate containing 100 g./l of active material.

In the case of various plants such as beans, tomatoes, maize, cotton, sunflower, gherkin and chrysanthemum, in the 2- to 4-leaf stage, as well as in the case of the fruit trees, the leaves are treated by spraying with a solution containing from 0.001 g./l to 10g./l of the material to be tested. The biometric and morphological change in the plants is then noted at the end of 8 days, 25 days and 1 month and even at the end of 6 months in certain cases such as the fruit trees.

Another test makes it possible to measure the abscission or anti-abscission power of the compounds for various types of plants. In the case of beans, this test is carried out as follows: the stem of the beans is cut at the level of the pot, the petioles are also cut at a distance of 2 cm from the stem, and the stem is dipped into a flanged tube containing a nutrient solution and the compound to be tested, at concentrations of $10^{-4}$ to $10^{-5}$ mol/liter. Every day from the 2nd day onwards the natural fall of the remaining 2 cm and the long stumps fall under 3 grams and 5 grams tension is observed and compared with the results obtained in the case of a comparison product.

Using these methods, several modes of action of the products which form the subject of the invention on the growth of the plants are studied in the examples which follow.

EXAMPLE I. REDUCTION IN HEIGHT

The height of the aerial parts and the distances between nodes of the treated plants are measured relative to comparison plants.

Under these conditions it is found in the case of beans (Contender variety) that, at doses of between 1 g./l and 0.01 g./l, the compounds 2, 33, 35, 43, 45 and 56 cause an increase in height of 10 to 20%. In contrast, at the same doses, the compounds 7, 13, 18, 19, 22, 31, 38 and 57 cause reductions in height of 10 to 20%. DL-Methionine has no effect on these plants.

EXAMPLE II. ABSCISSION OF THE PETIOLES

The test is carried out by counting the number of stumps which have fallen, in the case of beans (Contender variety), which makes it possible to assess the properties of the active materials in respect of accelerating or retarding the fall of leaves and of fruit.

Under these conditions it is found that at doses of $10^{-4}$ mol/liter the compounds 18, 2, 20 and 21 favour the abscission of the petioles; the compound No. 18 causes 100% abscission of the petioles in 48 hours; the compounds No. 2, 20 and 21 cause 100% abscission of the petioles after 5 days; the compounds No. 1, 3, 12, 16, 24, 44 and 52 exhibit an anti-abscission action and retard the natural fall of the petioles by about 10 days.

EXAMPLE III. ACTION ON FLOWERING

To carry out the test, the number of flowers of the treated plants is noted relative to an untreated comparison plant. This test is carried out in the case of beans of the Contender variety. The advancement or retardation in flowering is also observed.

Under these conditions it is found that: at doses of between 0.01 and 1 g./l, compounds No. 18, 20, 25, 35, 39, 45 and 53 increase the number of flowers by from 20 to 50%; at the same doses, the compounds No. 1, 2, 4, 9, 21, 23, 27, 32, 36, 47 and 56 increase the number of flowers by 15 to 20%; at doses of 0.1 to 0.001 g/l, compounds No. 16 and 34 reduce the number of flowers by 20 to 50%.

EXAMPLE IV. ACTION ON FRUITING

To carry out the test, the weight and the number of fruit of the treated plants are observed relative to an untreated comparison plant. This test is carried out in the case of beans of the Contender variety.

At a dose of 0.1 g/l, compound No. 56 causes an increase of 90% in the weight of the fruit.

At a dose of 0.01 g/l, compound No. 35 causes an increase of 60% in the weight of the fruit. At a dose of 0.1 g/l it causes an increase of 33% in the weight of the fruit.

At doses of between 0.01 g/l and 1 g/l, compounds No. 2, 7, 14, 20, 21, 25, 26, 27, 39, 43, 45, 47, 60 and 61 cause an increase in weight ranging from 20 to 50%.

At doses of between 0.01 g/l and 1 g/l, compounds No. 7, 13, 20, 26, 27, 30, 36 and 39 cause an increase of 15 to 50% in the number of fruit.

At doses of between 0.01 g/l and 1 g/l, compounds No. 3, 4, 8, 9, 19, 22, 23, 24, 28, 30, 32, 34, 38, 40, 42, 48, 49, 51, 57 and 58 cause a reduction of 10 to 50% in the weight of the fruit.

These examples show clearly that the remarkable properties of the compounds according to the invention, which can thus be used on all kinds of plants, such as large-scale and commercial-scale cultures, cereals, fruits, vegetables, ornamental plants, medicinal plants and perfume plants, in order to increase the yields, facilitate harvesting, for example by abscission of the leaves, hasten the ripening of the fruit, favour branching, alter the habit, cause floral induction (formation of flowers), retard flowering so as to combat the effect of frosts, reduce the height of the plants so as to obtain more compact plants, and the like.

The doses which can be used vary within wide limits in accordance with the desired effect, the species of the plant, the stage at which it is treated, the soil and the climatic conditions. In general, doses of between 0.001 g/l and 10 g/l are very suitable.

For their use in practice, the compounds according to the invention are rarely used by themselves. Most frequently, they form part of compositions which in general comprise a carrier and/or a surface-active agent in addition to the active material according to the invention.

The term "carrier" in the sense of the present description denotes an organic or inorganic, natural or synthetic material with which the active material is associated so as to facilitate its application to the plant, to the seed or to the soil or its transport or its handling. The carrier can be solid (clays, natural or synthetic silicates, resins, waxes, solid fertilisers and the like) or fluid (water, alcohols, ketones, petroleum fractions, chlorinated hydrocarbons and liquefied gases).

The surface-active agent can be an emulsifier, dispersing agent or wetting agent, which can be ionic or nonionic. Examples which may be mentioned are salts of polyacrylic acids and of ligninsulphonic acids and condensates of ethylene oxide with fatty alcohols, fatty acids or fatty amines.

The compositions according to the invention can be prepared in the form of wettable powders, dusting powders, granules, solutions, emulsifiable concentrates, emulsions, suspension concentrates and aerosols.

The wettable powders according to the invention can be prepared so that they contain from 20 to 95% by weight of active material, and they usually contain, in addition to a solid carrier, from 0 to 5% of a wetting agent, from 3 to 10% by weight of a dispersing agent and, where necessary, from 0 to 10% by weight of one or more stabilisers and/or other additives, such as penetrating agents, adhesives or anti-caking agents, dyestuffs and the like.

By way of example, the following is a composition of a wettable powder, the percentages being expressed by weight:

| | |
|---|---|
| active material | 50% |
| calcium lignosulphate (deflocculating agent) | 5% |
| isopropylnaphthalenesulphonate (wetting agent) | 1% |
| anti-caking silica | 5% |
| kaolin filler | 39% |

The emulsifiable concentrates which can be applied by spraying usually contain, in addition to the solvent and, where necessary, a co-solvent, from 10 to 50% by weight/volume of active material, and from 12 to 20% by weight/volume of appropriate additives, such as stabilisers, penetrating agents, corrosion inhibitors, dyestuffs and adhesives.

The suspension of concentrates, which can also be applied by spraying, are prepared so that a fluid stable product is obtained which does not settle out, and which usually contains from 10 to 75% by weight of active material, from 0.5 to 15% by weight of surface-active agent, from 0.1 to 10% by weight of anti-sedimentation agents such as protective colloids and thixotropic agents, and from 0 to 10% by weight of appropriate additives such as anti-foaming agents, corrosion inhibitors, stabilisers, penetrating agents and adhesives, and, as the carrier, water or an organic liquid in which the active material is substantially insoluble; certain organic solid materials or inorganic salts can be dissolved in the carrier so as to help in preventing sedimentation or to act as anti-freeze agents for water.

Aqueous dispersions and emulsions, for example compositions obtained by diluting a wettable powder or an emulsifiable concentrate according to the invention with water fall within the general scope of the present invention. These emulsions can be of the water-in-oil type or of the oil-in-water type and can have a thick consistency such as that of a "mayonnaise".

The compositions according to the invention can contain other ingredients, for example protective colloids, adhesives or thickeners, thixotropic agents, stabilisers or sequestering agents, as well as other known active materials having pesticidal properties, in particular insecticides, fungicides or growth regulators.

All these compositions can be applied to the plants by various methods such as spraying onto the aerial part of the plants, dipping of seeds, plants, root-balls, roots or fruit, watering of the soil, injection into the plant and the like.

We claim:

1. A plant growth-regulating composition comprising an agricultural carrier; and, as the active material, a plant growth-regulating effective amount, in the range of from about 0.001 g/l to about 10 g/l, or when in wettable powder form from about 20 to about 95% by weight of active material, or when in concentrate suspension form from about 10 to about 75% of active material, or when in emulsifiable concentrate form from about 10 to about 50% weight/volume of active material, of at least one compound of the formula:

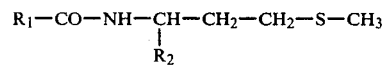

in which:

R₁ represents a hydrogen atom, a ($C_2$ to $C_{20}$) alkyl radical, a halogenated ($C_1$ to $C_{20}$) alkyl radical, an optionally halogenated ($C_3$ to $C_6$) cycloalkyl radical, an optionally halogenated ($C_2$ to $C_{20}$) alkenyl radical, an optionally halogenated phenylalkenyl or phenyloxyalkenyl radical (with a $C_2$ to $C_4$ alkenyl part), a phenyl or naphthyl radical optionally substituted by one or more identical or different atoms or radicals from amongst halogen atoms, ($C_1$ to $C_4$) alkyl radicals, trifluoromethyl, nitro, cyano, m-trifluoromethyl-benzoyl and o-, m-, or p-fluorobenzoyl substituted amino, hydroxyl, alkoxy (with a $C_1$ to $C_4$ alkyl part), aminosulphonyl or alkoxycarbonyl (with a $C_1$ to $C_4$ alkyl part), or a heterocyclic radical selected from the group consisting of furyl and pyridyl, and R₂ represents a carboxylic acid group or a salt which this group can form with an inorganic base or with a primary, secondary or tertiary amine, a

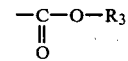

group, in which R₃ is a ($C_1$ to $C_4$) alkyl radical optionally substituted by one or more hydroxyl groups, a —CN group or a

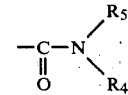

group in which R₄ and R₅, which may be identical or different, represent a hydrogen atom or a ($C_1$ to $C_4$) alkyl radical with the proviso that when said composition is in solution form, it further comprises a surface active agent.

2. A composition according to claim 1, wherein said active material is at least one compound of the formula:

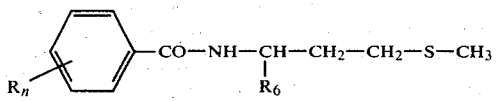

in which:
  $R_n$ represents from one to three identical or different atoms or radicals chosen from amongst halogen atoms and ($C_1$ to $C_4$) alkyl, trifluoromethyl, nitro, m-trifluoromethyl-benzoyl and o-, m-, or p-fluorobenzoyl acrylated amino, hydroxyl, alkoxy (with a $C_1$ to $C_4$ alkyl part) or alkylcarbonyloxy (with a $C_1$ to $C_4$ alkyl part) radicals and
  $R_6$ represents a carboxylic acid group or a salt which this group can form with an inorganic base with a primary, secondary or tertiary amine a

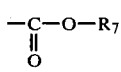

group in which $R_7$ is a $C_1$ to $C_4$ alkyl radical, a

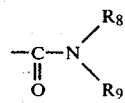

group in which $R_8$ and $R_9$, which may be identical or different, are a hydrogen atom or a methyl or ethyl radical, or a —CN group.

3. A composition according to claim 2, wherein said active material is at least one compound of the formula:

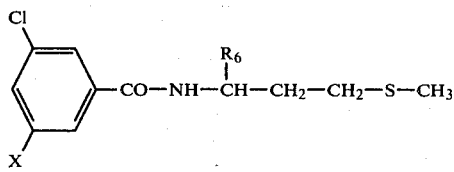

in which $R_6$ has the same meaning as in claim 2 and X represents a chlorine atom or a hydrogen atom.

4. A composition according to claim 2, wherein $R_6$ is a carboxylic acid group or a salt obtained by the action of the said acid on an inorganic base, or a —CO—O—$R_7$ group wherein $R_7$ is a $C_1$ to $C_4$ alkyl.

5. A composition according to claim 1, wherein said compound is a derivative of 4-methylthio-butyric acid in which the $R_1$-CO-NH is a member of the group consisting of
  (D,L)-2-(3′,5′-dichloro-benzamido);
  (D,L)-2(4′-chloro-cinnamido);
  (D,L)-2-benzamido;
  (D,L)-2-(2′-chloro-benzamido);
  (D,L)-2-(2′-fluoro-benzamido);
  (D,L)-2-(3′-chloro-benzamido);
  (D,L)-2-(3′-bromo-benzamido);
  (D,L)-2-(4′-fluoro-benzamido);
  (D,L)-2-(2′,4′-dichloro-benzamido);
  (D,L)-2-(2′,5′-dichloro-benzamido);
  (D,L)-2-(3′-chloro-4′-fluoro-benzamido);
  (D,L)-2-(2′-methyl-benzamido);
  (D,L)-2-(3′-methyl-benzamido);
  (D,L)-2-(4′-t-butyl-benzamido);
  (D,L)-2-(2′-methoxy-benzamido);
  (D,L)-2-(3′-trifluoromethyl-benzamido);
  (D,L)-2-(2′-nitro-benzamido);
  (D,L)-2-(3′-nitro-benzamido);
  (D,L)-2-(3′-chloro-4′-isopropyl-benzamido);
  (D,L)-2-(2′,5′-dihydroxy-benzamido);
  (D,L)-2-(2′-hydroxy-5′-methoxy-benzamido);
  (D,L)-2-(2′,5′-di-acetoxy-benzamido);
  (D,L)-2-(2′,3′-di-acetoxy-benzamido);
  (D,L)-2-(2′-hydroxy-3′-methyl-benzamido);
  (D,L)-2-(2′-hydroxy-5′-bromo-benzamido);
  (D,L)-2-(-2′-methoxy-5′-aminosulfonyl-benzamido);
  (D,L)-2-(naphthamido-1′);
  (D,L)-2-[-2′hydroxy-5′-(m-trifluoromethyl-benzamido)benzamido];
  (D,L)-2-[-2′-hydroxy-5′-(m-fluoro-benzamido)benzamido];
  (D,L)-2-[-2′-hydroxy-5′-(p-fluoro-benzamido)benzamido];
  (D,L)-2-[-2′-hydroxy-4′-(o-fluoro-benzamido)benzamido]; and
  (D,L)-2-(cinnamido).

6. A composition according to claim 1, wherein the active compound is (D,L)-2-(3′,5′-dichlorobenzamido)-4-methylthiobutyric acid.

7. A composition according to claim 1, wherein the active compound is (D,L)-2-(3′-chloro-benzamido)-4-methylthio-butyric acid.

8. A composition according to claim 1, wherein the active compound is (D,L)-ethyl-2-(3′,5′-dichlorobenzamido)-4-methylthiobutyrate.

9. A composition according to claim 1, wherein the active compound is (D,L)-ethyl-2-(cinnamido)-4-methylthiobutyrate.

10. A composition according to claim 1, wherein the active compound is (D,L)-ethyl-2-(3′-chloro-benzamido)-4-methylthiobutyrate.

11. A composition according to claim 1, wherein the active compound has as $R_1$ the group

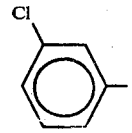

and as $R_2$ the —CN group.

12. A composition according to claim 1, wherein said compound is an ester of 4-methyl thiobutyric acid in which the $R_1$—CO—NH is a member of the group consisting of
  (D,L)-ethyl-2-(3′,5′-dichlorobenzamido);
  (D,L)-ethyl-2-(cinnamido);
  (D,L)-ethyl-2-(2′-chlorobenzamido);
  (D,L)-ethyl-2-(3′-chloro-benzamido);
  (D,L)-ethyl-2-(3′-chloro-4′-fluoro-benzamido);
  (D,L)-methyl-2-(2′-hydroxy-benzamido);
  (D,L)-ethyl-2-(-3′-nitro-benzamido);
  (D,L)-ethyl-2-(-2′-methoxy-5′-aminosulfonyl);
  (D,L)-ethyl-2-[2′-hydroxy-5′-(o-fluoro-benzamido)-benzamido]; and
  (D,L)-n-butyl-2-(3′,5′-dichlorobenzamido).

13. A process for modifying the growth of plants comprising applying to said plants a growth-modifying-effective amount of a plant growth-regulating compound of the formula

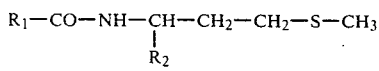

in which:
- $R_1$ represents a hydrogen atom, an optionally halogenated ($C_1$ to $C_{20}$) alkyl radical, an optionally halogenated ($C_3$ to $C_6$) cycloalkyl radical, an optionally halogenated ($C_2$ to $C_{20}$) alkenyl radical, an optionally halogenated phenylalkenyl or phenyloxyalkenyl radical (with a $C_2$ to $C_4$ alkenyl part), a phenyl or naphthyl radical optionally substituted by one or more identical or different atoms or radicals from amongst halogen atoms, ($C_1$ to $C_4$) alkyl radicals, trifluoromethyl, nitro, cyano, m-trifluoromethyl-benzoyl and o-, m-, or p-fluorobenzoyl substituted amino, hydroxyl, alkoxy (with a $C_1$ to $C_4$ alkyl part), aminosulphonyl or alkoxycarbonyl (with a $C_1$ to $C_4$ alkyl part), or a heterocyclic radical selected from the group consisting of furyl and pyridyl, and
- $R_2$ represents a carboxylic acid group or a salt which this group can form with an inorganic base or with a primary, secondary or tertiary amine, a

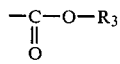

group, in which $R_3$ is a ($C_1$ to $C_4$) alkyl radical optionally substituted by one or more hydroxyl groups, a —CN group or a

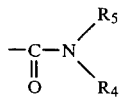

group in which $R_4$ and $R_5$, which may be identical or different, represent a hydrogen atom or a ($C_1$ to $C_4$) alkyl radical.

14. A process for regulating the growth of plants according to claim 13, wherein said compound is of the formula:

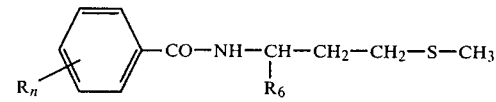

in which:
- $R_n$ represents from one to three identical or different atoms or radicals chosen from amongst halogen atoms and ($C_1$ to $C_4$) alkyl, trifluoromethyl, nitro, m-trifluoromethyl-benzoyl and o-, m-, or p-fluorobenzyl acrylated amino, hydroxyl, alkoxy (with a $C_1$ to $C_4$ alkyl part) or alkylcarbonyloxy (with a $C_1$ to $C_4$ alkyl part) radicals and
- $R_6$ represents a carboxylic acid group or a salt which this group can form with an inorganic base with a primary, secondary or tertiary amine a

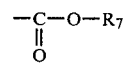

group in which $R_7$ is a $C_1$ to $C_4$ alkyl radical, a

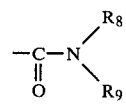

group in which $R_8$ and $R_9$, which may be identical or different, are a hydrogen atom or a methyl or ethyl radical, or a —CN group.

15. A process for regulating the growth of plants according to claim 13, wherein said compound is of the formula:

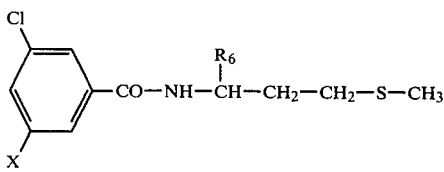

in which $R_6$ has the same meaning as in claim 29 and X represents a chlorine atom or a hydrogen atom.

* * * * *